United States Patent [19]
Whisson

[11] Patent Number: 5,762,633
[45] Date of Patent: Jun. 9, 1998

[54] SYRINGE OR LIKE PARENTERAL DEVICE

[75] Inventor: Maxwell Edmund Whisson, Perth, Australia

[73] Assignee: Eastland Technology Australia PTY, Ltd., Western Australia, Australia

[21] Appl. No.: 619,680
[22] PCT Filed: Oct. 11, 1994
[86] PCT No.: PCT/AU94/00618
 § 371 Date: Mar. 29, 1996
 § 102(e) Date: Mar. 29, 1996
[87] PCT Pub. No.: WO95/11712
 PCT Pub. Date: May 4, 1995

[30] Foreign Application Priority Data
Oct. 26, 1993 [AU] Australia ............... PM2039

[51] Int. Cl.$^6$ .................................. A61M 37/00
[52] U.S. Cl. .................................. 604/187
[58] Field of Search ............... 604/187, 191, 604/218, 222, 223, 227, 210

[56] References Cited

U.S. PATENT DOCUMENTS

| | | |
|---|---|---|
| 2,475,060 | 7/1949 | Smith . |
| 3,368,558 | 2/1968 | Sarnoff et al. . |
| 3,587,575 | 6/1971 | Lichtenstein . |
| 4,314,556 | 2/1982 | Ma ............... 604/187 |
| 5,032,117 | 7/1991 | Motta ............ 604/187 |

FOREIGN PATENT DOCUMENTS

| | | |
|---|---|---|
| 2 064 964 | 6/1981 | United Kingdom . |
| WO 90/05555 | 5/1990 | WIPO . |
| WO 91/00747 | 1/1991 | WIPO . |
| WO 93/20872 | 10/1992 | WIPO . |

*Primary Examiner*—Michael Buiz
*Assistant Examiner*—Kevin Truong
*Attorney, Agent, or Firm*—Merchant, Gould, Smith, Edell, Welter & Schmidt, P.A.

[57] ABSTRACT

A syringe or like device which can be used for the conveyance of parenteral fluids which are to be introduced into or drawn from the body through the skin comprising a tubular body (11) having a forward end (26) and a rearward end (34) where the forward end is capable of receiving a hollow needle (20) to enable the needle to be able to project from the body, the needle (20) slidable relative to the body (11), the body (11) also including a chamber (14) capable of receiving a parenteral fluid and capable of being reduced in volume to expel the fluid contained therein, the needle (20) is capable of being manually retracted into the body (11) by a retracting member (28) such that the chamber reduces in volume to expel the fluid contained therein and such that the needle (20) is retracted to be wholly contained within the body (11). The needle is able to be supported at one end from the body by a plug (16) which is slidably and sealingly received in the body (11). The chamber (14) is located rearward of the plug (16) and the plug is adapted to enable the needle to communicate with the chamber (14) through the plug, a stop (18) provided in the body rearward of the plug (16) to define the rearward end of the chamber (14). The stop (18) being slidably and sealingly received in the body (11) whereby a greater degree of forces required to move the stop (18) than to move the plug (16). The rearward end (34) of the body slidably supporting a slider (38) or axial movement, an external protrusion (40) on the slider (38) for manipulation of the slider to effect axial movement. The retracting member (28) comprising a flexible member secured at one end to the plug (16) and secured at the other end to the slider (38) slidably and sealingly received through the stop (18).

24 Claims, 11 Drawing Sheets

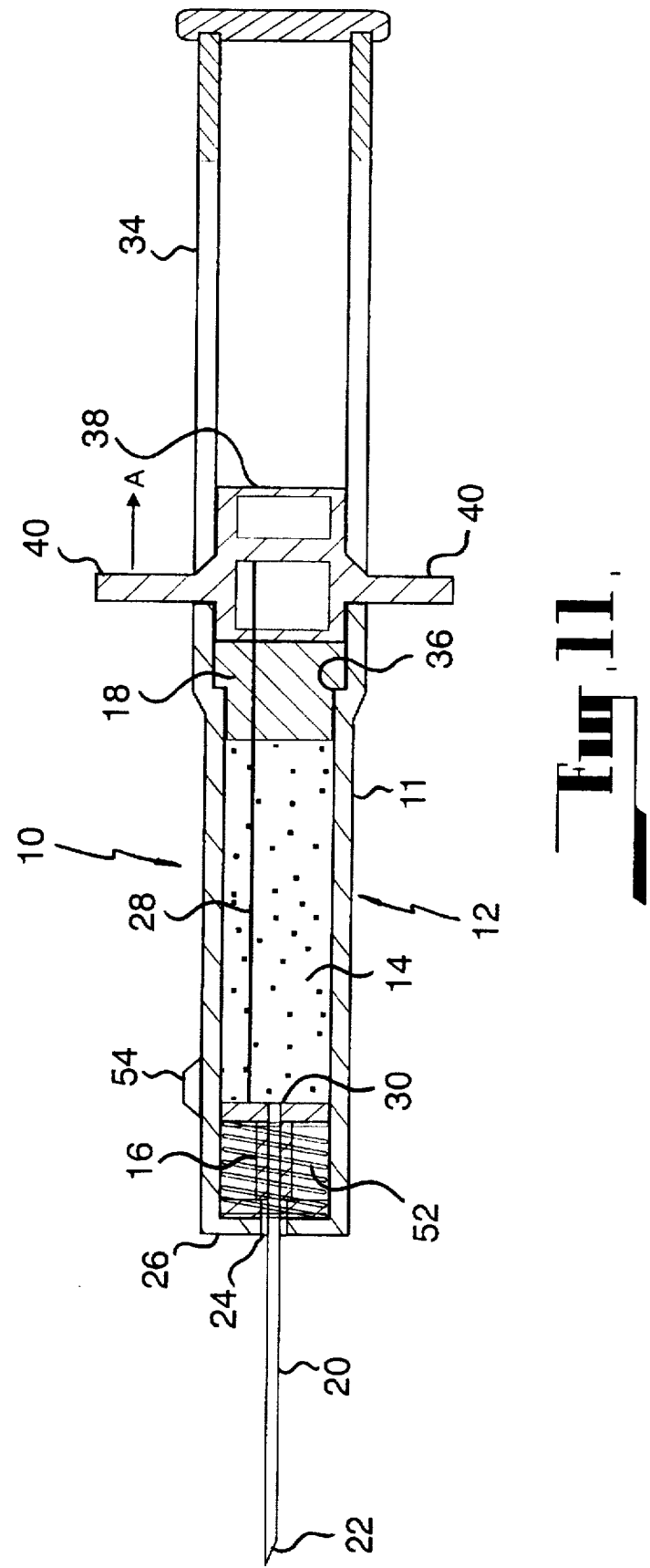

SYRINGE OR LIKE PARENTERAL DEVICE

FIELD OF INVENTION

This application is a 371 of PCT/AU94/00618 Oct. 11, 1994

THIS INVENTION relates to a syringe or like parenteral device.

Throughout this specification the term "syringe or like device" shall be taken to include any device which can be used for the conveyance of parenteral fluids which are to be introduced into or drawn from the body through the skin and shall include within its scope a syringe, a cannula, a hypodermic needle, an intravenous infusion line, and like devices.

BACKGROUND OF THE INVENTION

A primary characteristic of parenteral devices is the provision of a sharp hollow needle to facilitate the transfer of fluids to or from the body. The difficulty created by the presence of such a needle arises from the possibility of injury which may be caused to a user or to medical staff when using the device, or indeed to any person who may be required to handle the device before or after use.

Of course, the injury itself does not represent the major concern. The major concern arising from the dangers of infection from such injuries is due to the pathogens which may be present on the needle as a result of its use. Indeed, it has been proven that a number of viral infections, notably the HIV virus and hepatitis B, can be transmitted by the reuse of needles previously used to inject an infected individual.

These dangers have resulted in the development of very careful and sometimes detailed disposal procedures being adopted in institutions where such parenteral devices are used. It has also resulted in attempts being made at developing single use parenteral devices that are not capable of being reused.

However, the disposal procedures adopted by such institutions are not able to be enforced in out-of-clinic situations, such as those situations where individuals inject recreational drugs. Further, the users of recreational drugs are often capable of quite easily manipulating a so called "one use" syringe to be able to continue using that same syringe.

SUMMARY OF THE INVENTION

It is an object of the present invention to provide an improved parenteral device wherein operation of the device in performing an injection alters the configuration of the device such that the device becomes extremely difficult to refill and also to reuse. A further object is to provide a parenteral device having a needle that retracts so as not to be exposed after use.

The present invention provides a syringe or like device comprising a tubular body having a forward end and a rearward end, the forward end being capable of receiving a hollow needle therein so as to be able to project therefrom, the retractable needle being slidable relative to the body, the body also including a chamber capable of receiving parenteral fluid and capable of being reduced in volume to expel fluid contained therein, wherein; the needle is capable of being manually retracted within the body by a retracting means such that the chamber reduces in volume to expel fluid contained therein and such that the needle is retracted to be wholly contained within the body; the needle is supported at one end from the body by a plug, the plug being configured to be sealingly engaged with the internal walls of the body and to be slidable within the body; the chamber is located rearwardly of the plug and the plug is adapted to enable the needle to communicate with the chamber through the plug; a stop is provided in the body rearward of the plug to define the rear end of the chamber, the stop means being slidable relative to the body and being in sealing engagement with the internal walls of the body, whereby a greater degree of force is required to move the stop than to move the plug; the rearward end of the body slidably supporting a slider for axial slidable movement, a protrusion on said slider for manipulation thereof to effect said axial movement, wherein said retracting means comprises a flexible member, secured at one end to the plug and secured at its other end to the slider and slidably and sealingly received through the stop.

By holding the forward end of the body of the syringe closely adjacent the skin of the user, the needle may continue to be retracted into the body of the device during injection such that the sharp end of the needle is not caused to be exposed whatsoever between insertion of the needle into the body and completion of the injection.

When using the parenteral device of this invention it thus becomes important to use the device accurately to ensure that the dose is delivered subcutaneously. Thus, the initial retracting of the needle causes the volume of the chamber to reduce so as to expel the fluid therefrom, to a point where the plug abuts the stop means. Further retraction of the needle then causes the rearward movement of both the plug and the stop means to allow the needle to be fully withdrawn into the body. A greater degree of force is required to move the stop means than to expel the fluid.

The present invention provides an improved parenteral device that allows for the complete retraction of its needle during use within the body thereof. The lack of any externally operable rigid elements which are rigidly connected to the needle and that may allow the re-extension of the needle assists in causing the device to be primarily a one use device. The construction of the device is simple and cheap and allows for relatively easy filling with minimal complexity. Further, it is expected that as the injection of parenteral fluid and withdrawal of the needle occurs simultaneously, there may be the additional beneficial effect of depositing the parenteral fluid throughout the deeper part of the needle track. This is expected to provide an advantage in reducing the pain which may be caused in conventional syringes by the distension of tissues at the single point of injection and more rapid absorption of the fluid.

It will also be appreciated that the dimensions and extent of travel of the needle and plug may be optimised for expelling a parenteral fluid into any body cavity. In particular, the needle may be inserted into a vein and retracted along the lumen of the vein as the parenteral fluid is expelled, the chamber being completely emptied before the needle is retracted out of the vein.

According to a preferred feature of the invention, the stop when defining the rearward end of the chamber is sealingly and slidably received in the body and on completion of the movement of the plug to the minimum volume position of the chamber, the stop is movable with the plug whereby the stop will be accommodated in a non sealing manner in the rearward end. The sealing engagement can be effected by forming the rearward end of the body with a greater internal diameter than the remainder of the body. Alternatively the cross-sectional configuration of the rearward end may be formed with a portion having a greater transverse dimension than the diameter of the remainder of the body. This can be achieved by formation of a longitudinal groove in the internal wall of rearward end of the body. In addition, if desired the plug when at its rearmost position is non sealingly engaged in the rearward end of the body. As a further alternative the rearward end of the body can have a different cross-sectional configuration to that of the body. For example, the body may be of circular cross-section and the rearward end may be of square or eliptical cross-section.

According to a further alternative preferred feature of the invention the protrusion comprises an axially directed shaft which can take the same form as the handle of a plunger of a conventional syringe. Alternatively the external protrusion may comprise a radially directed protrusion extending laterally from the side wall of the rearward end.

According to a further preferred feature of the invention, a protrusion is provided on the interior of the body which is engaged by the sealing surface of the stop and/or the plug on joint rearward movement of the stop and plug to cause damage to the sealing surface. As an alternative feature, the protrusion may pierce the stop and/or plug on joint rearward movement of the stop and plug to destroy the sealing integrity of the stop and/or plug.

According to a further preferred feature of the invention, free end of the needle is received in a nipple-like element which is provided at the forward most end of the body and whereby manual withdrawal of the nipple-like element away for the body will cause extension of the needle within said body, whereby the nipple-like element is capable of being removed from the needle. A further feature of the feature, the nipple-like element is provided with a port which is engagable with a receptacle of a parenteral agent such as an ampoule and the opening in the free end of the needle opens into the port.

According to a further preferred feature of the invention, a resilient means is provided between the body and the plug and is associated with a trigger means whereby when the needle is in the extended position the resilient means is maintained in a stressed state and on release of the trigger mechanism the resilient means is able to move to an unstressed state and cause movement of the needle, plug and stop to the fully retracted position.

The present invention will now be described in relation to the accompanying drawings. However, it is to be appreciated that the following description is not to limit the generality of the above description.

BRIEF DESCRIPTION OF THE DRAWINGS

In the drawings:

FIG. 11 is a sectional view of a parenteral device according to a seventh embodiment of the invention.

DESCRIPTION OF THE PREFERRED EMBODIMENT

Figure 1:
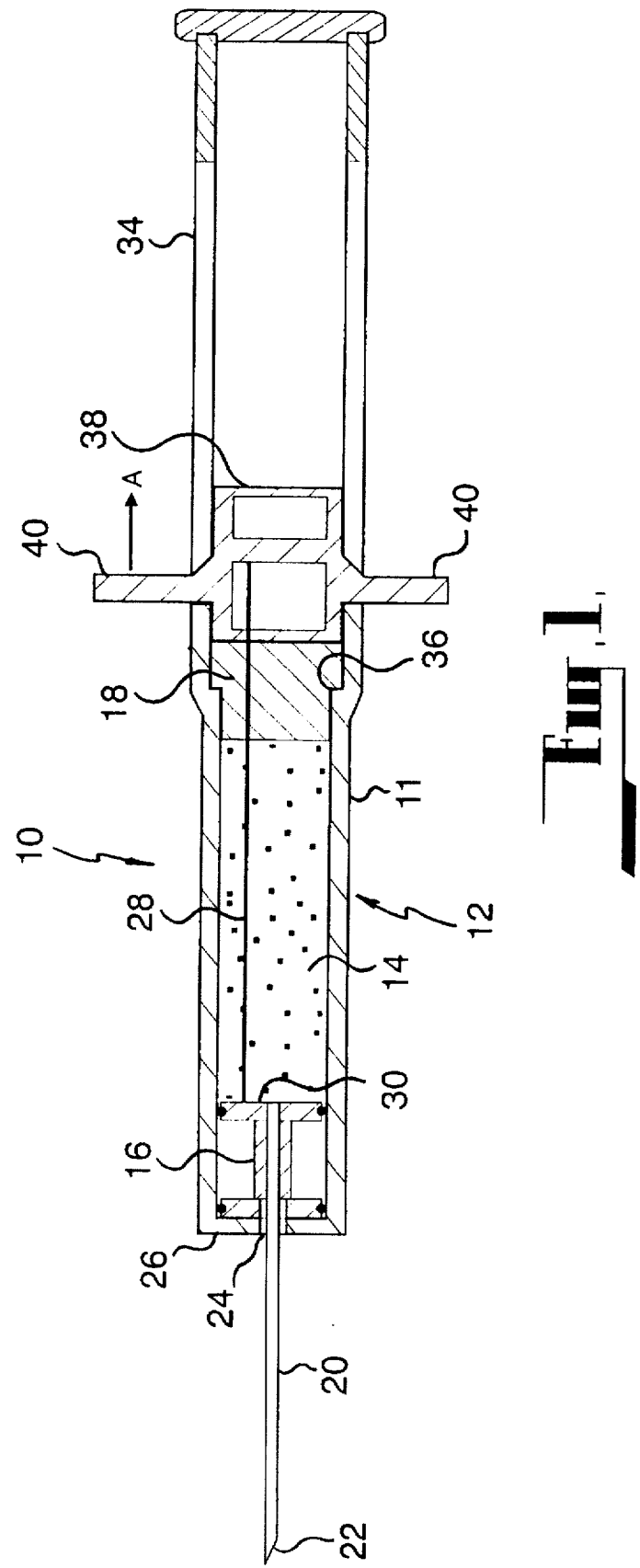
FIG. 1 is a sectional view of a parenteral device according to a first embodiment of the present invention with the chamber filled.

FIG. 1 illustrates a parenteral device 10 having a body 12 in the form of a substantially tubular barrel 11 which provides a sealed chamber 14 between a plug 16 and a stop 18. A sharpened tubular needle 20 is firmly fixed to the plug 16 and passes through it so as to provide fluid communication within the hollow interior of the needle 20 between the chamber 14 and the open end 22 of the needle 20. The needle 20 passes through an opening 24 in the forward end 26 of the body 12.

The body 12 further comprises an axial extension 34 which is of tubular configuration and is coaxial with the tubular barrel 12 but is of greater diameter to provide a step 36 at the junction between the tubular barrel and the axial extension. The stop 18 when in its normal position bridges the step 36 and is configured to be sealingly engaged with the bore of both the tubular barrel 12 and the axial extension 34.

The axial extension 34 slidably supports a slider 38 through a pair of diametrically opposed slots formed in the side wall of the axial extension. The slider comprises a main portion accommodated within the axial extension and a protruberance 40 to each side of the main body which extends through the slots. The protruberances provide a handle to enable movement of the slider 38 in the axial extension.

A retracting means in the form of a flexible member 28 is secured at one end to the rear 30 of the plug 16 and at the other end to the slider 38. The flexible member 28 passes through the stop 18 in sealing engagement therewith.

The chamber 14 is capable of receiving and containing a parenteral fluid such that by moving the slider 40 outwardly within the tubular extension, the plug 16 through its connection to the flexible member is moved to the rear of the body 12. This serves to retract the needle 20 into the main body and also in reducing the volume of the chamber 14 to expel the parenteral fluid from the open end 22 of the needle 20.

Figure 2:
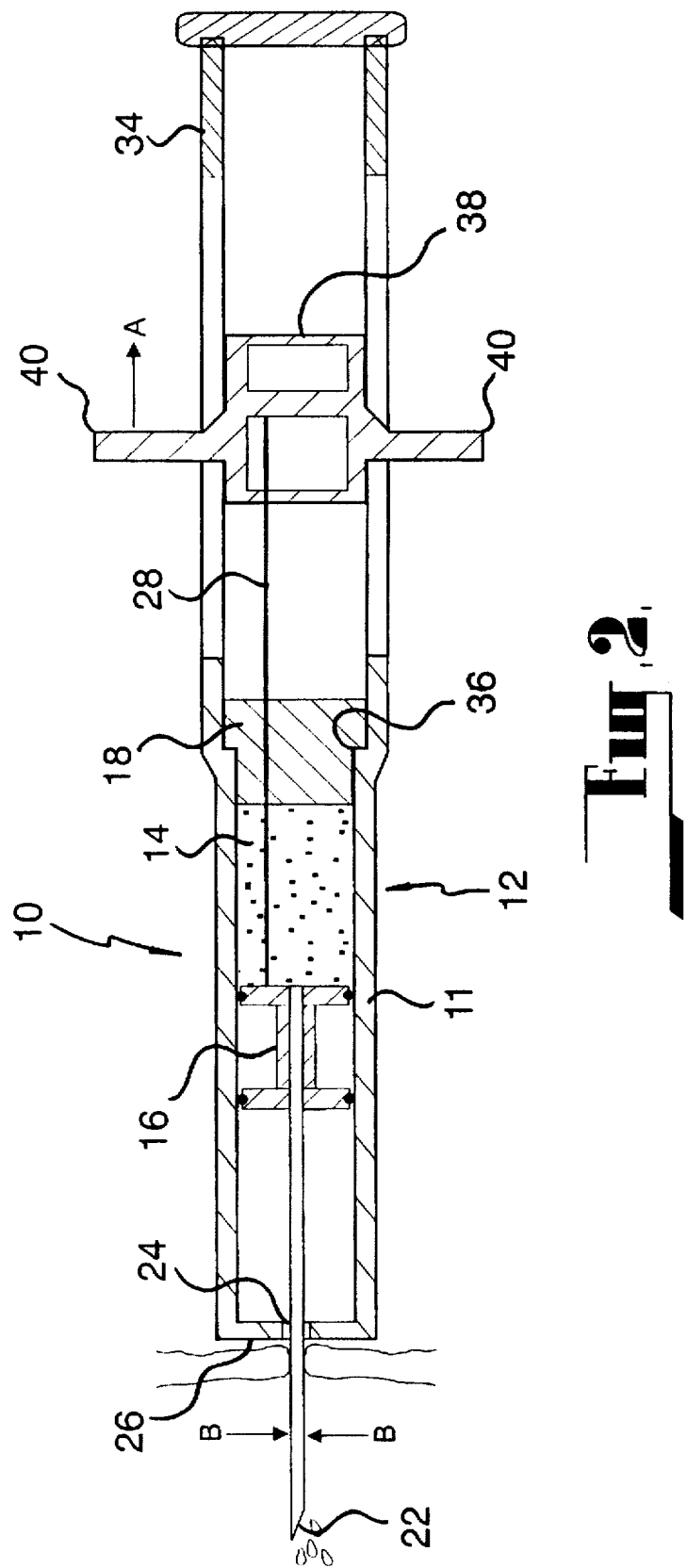
FIG. 2 is a sectional view of the embodiment of FIG. 1 during injection.

The device 10 is shown in use in FIG. 2 with the needle 20 having been inserted below the surface of the skin of a person. With the parenteral device 10 in this position, where its forward end 26 lies closely adjacent the skin, the slider 38 may be pulled in the direction of arrow A to reduce the volume of chamber 14 by urging the plug 16 towards the stop 18 to expel the parenteral fluid from the needle 20. As this occurs, the needle 20 is being withdrawn into the body 12 of the device 10. In this form, the device 10 is preferably configured such that all of the parenteral fluid is expelled from the chamber 14 by the time that the open end 22 of the needle 20 reaches point B which is about 5 mm below the surface of the skin.

Figure 3:
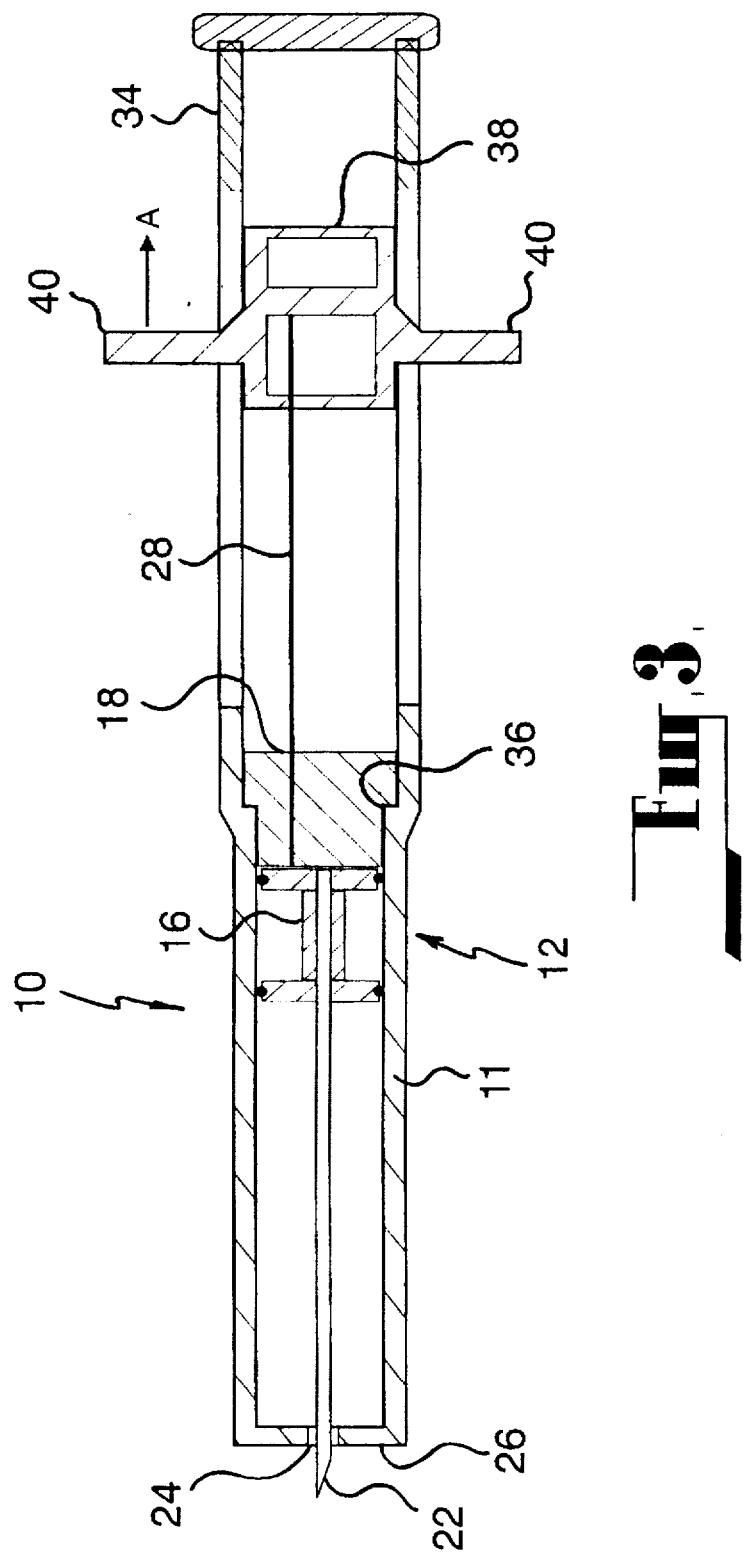
FIG. 3 is a sectional view of the embodiment of FIG. 1 after the chamber has been emptied.
Figure 4:
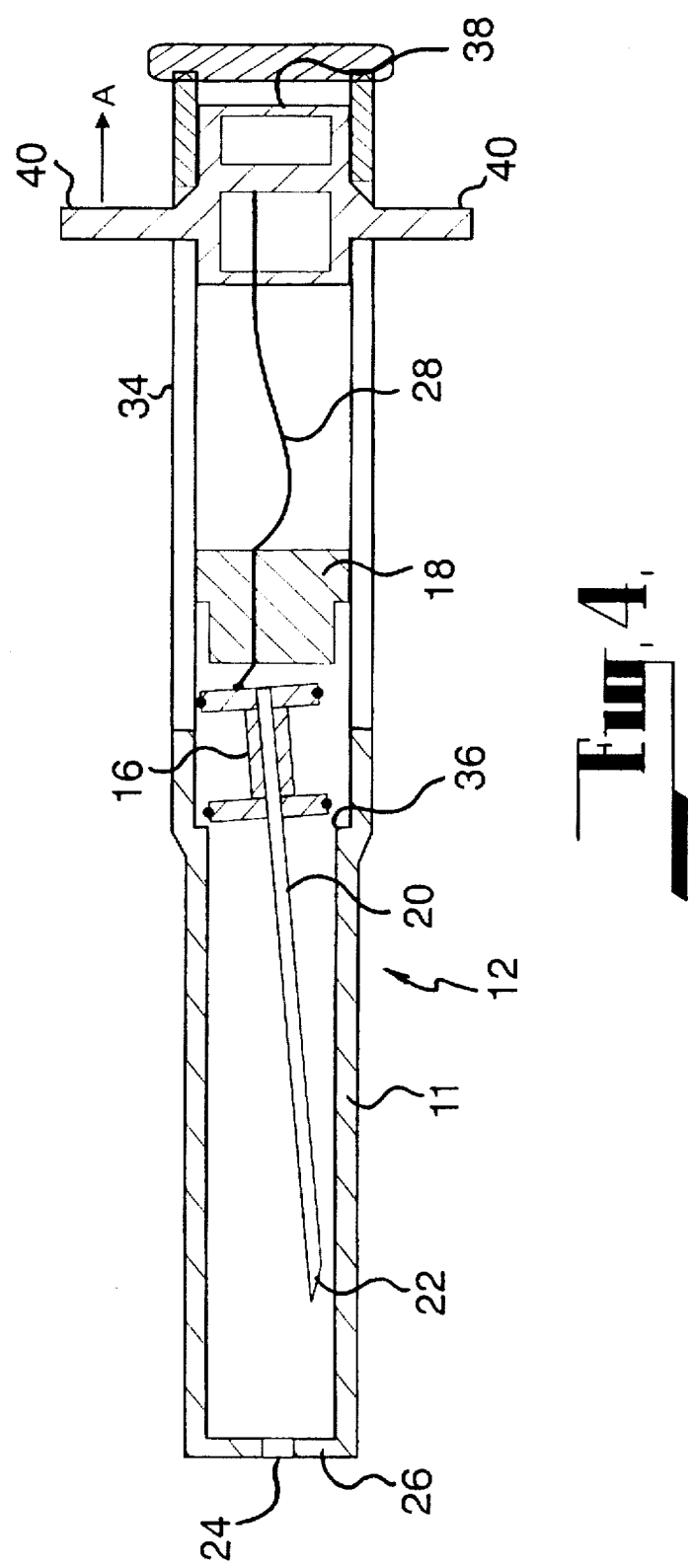
FIG. 4 is a sectional elevation of the embodiment of FIG. 1 ready for disposal.
Figure 7A:
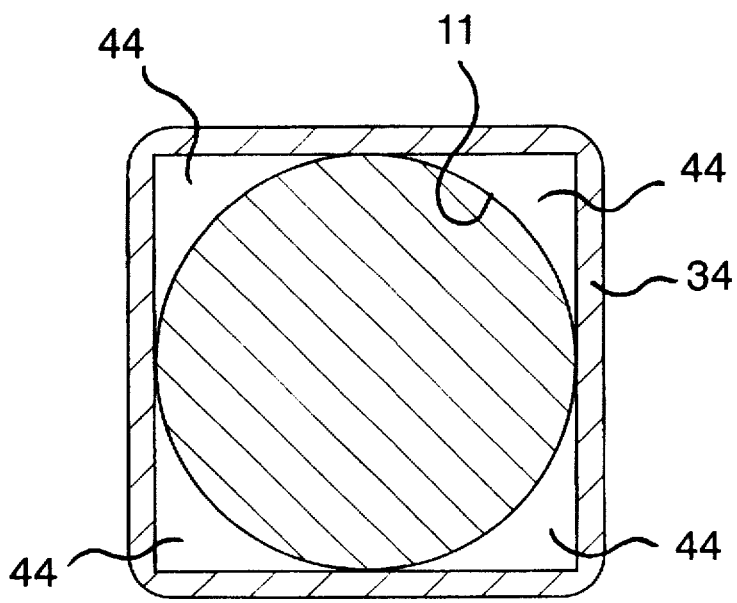
FIG. 7a and 7b are cross-section view of the axial extension of alternative embodiments of the invention as shown at FIG. 1.
Figure 7B:
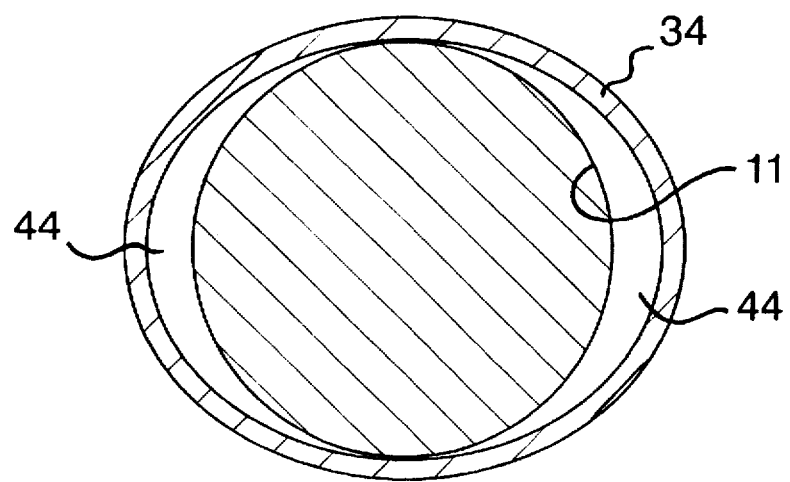

FIG. 3 illustrates the device 10 after all of the parenteral fluid has been expelled from the chamber 14. At this position, the flexible member 28 has been pulled through the stop 18 to a point where the chamber 14 has been fully reduced in volume and the plug 16 is in contact with the stop 18. On the application of a further force to the flexible member 28 the slidable stopping means 18 is urged towards the rear 34 of the body 12 such that the entire length of the needle 20 is retracted within the body 12. FIG. 4 illustrates the device after the needle 20 has been retracted completely within the body 12. The axial extension 34 provides a region of increased diameter within which the stop 18 is able to be received and the plug 16 is caused to enter and in which the plug is loosely received when the free end 22 of the needle lies inward of the opening 24. Since there is no rigid interconnection between the plug 16 and the slider 38 it is extremely difficult for a user to realign the plug 16 in the main body and cause the needle 20 to be extended to be able to reuse the syringe. The step 36 provides a sharp reduction in diameter of the bore of the body, so as to provide a well defined shoulder which creates a difficulty in reengaging the plug 16 in the tubular barrel 12. In a second and third embodiment in the invention as shown at FIGS. 7a and 7b respectively the internal cross-section of the axial extension 34 is formed to have a portion 44 of greater transverse dimensions than the cross-section of the tubular barrel 11 such that on the stop 18 and the plug 16 entering the axial extension 34 the sealing engagement with the internal wall of the body is lost. This increased transverse dimension can be achieved by having the axial extension formed to have the square crosssection as shown at FIG. 7a in relation to the second embodiment or alternatively an elliptical cross-section as shown at FIG. 7b in relation to the third embodiment.

Figure 8:
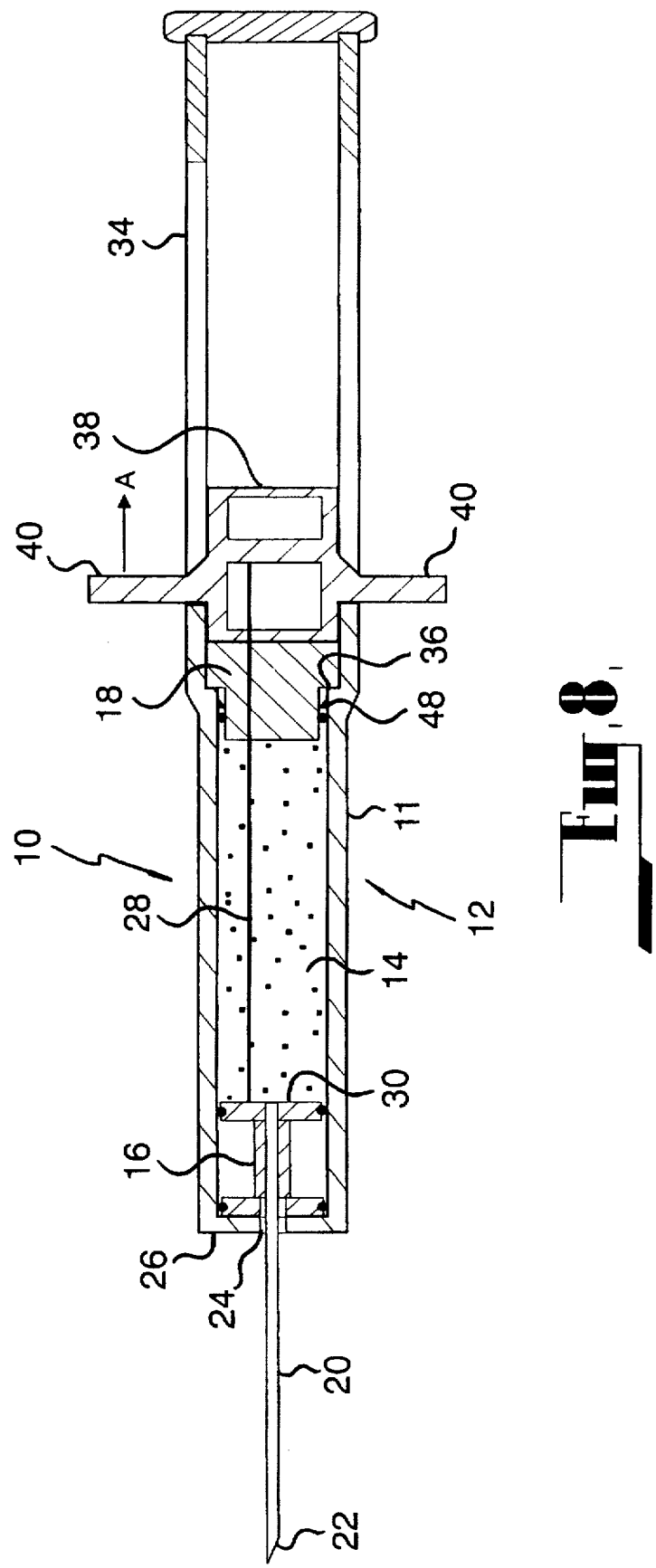
FIG. 8 is a sectional view of a parenteral device according to a fourth embodiment of the invention.

In a fourth embodiment as shown at FIG. 8, sharp projections 48 are formed on the inner wall of the body 12, which are intended to damage the sealing surfaces of the stop 18 and/or the plug on movement to a fully retracted position.

Figure 9:
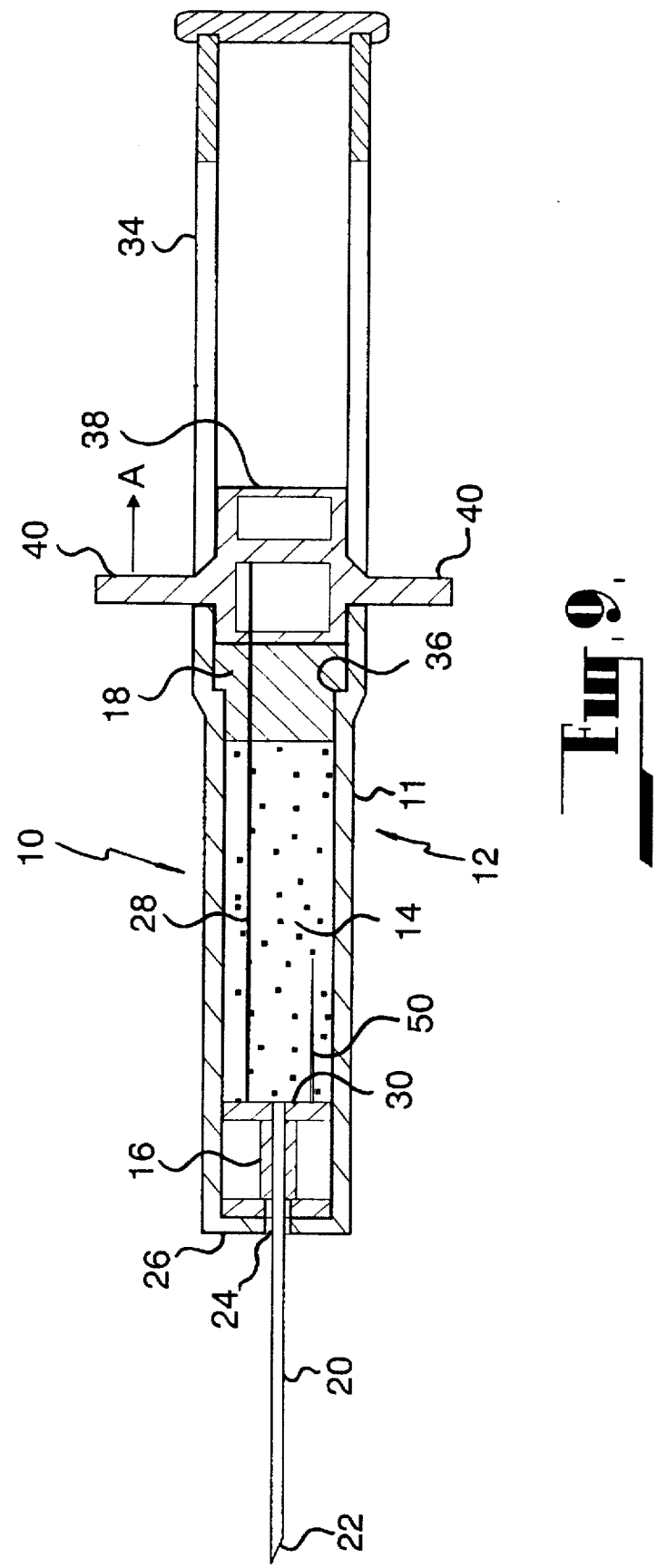
FIG. 9 is a sectional view of a parenteral device according to a fifth embodiment of the invention.
Figure 10:
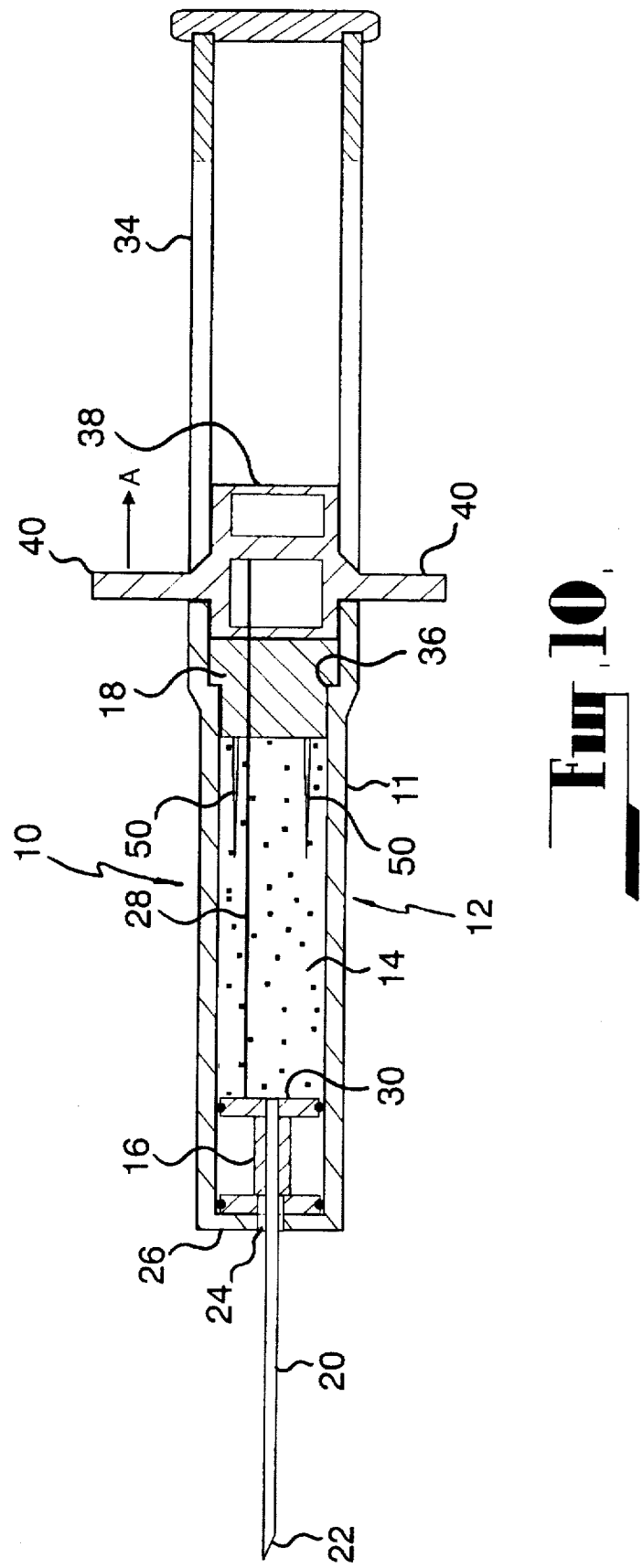
FIG. 10 is a sectional view of a parenteral device according to a sixth embodiment of the invention.

According to a fifth and sixth embodiment as shown at FIGS. 9 and 10 respectively, one or more spikes 50 or the like may be fitted to the plug 16 or stop means 18 which will pierce the stop 18, or plug 16 respectively on their coming into an abutting relationship to destroy the sealed nature of the chamber 14.

Figure 5:
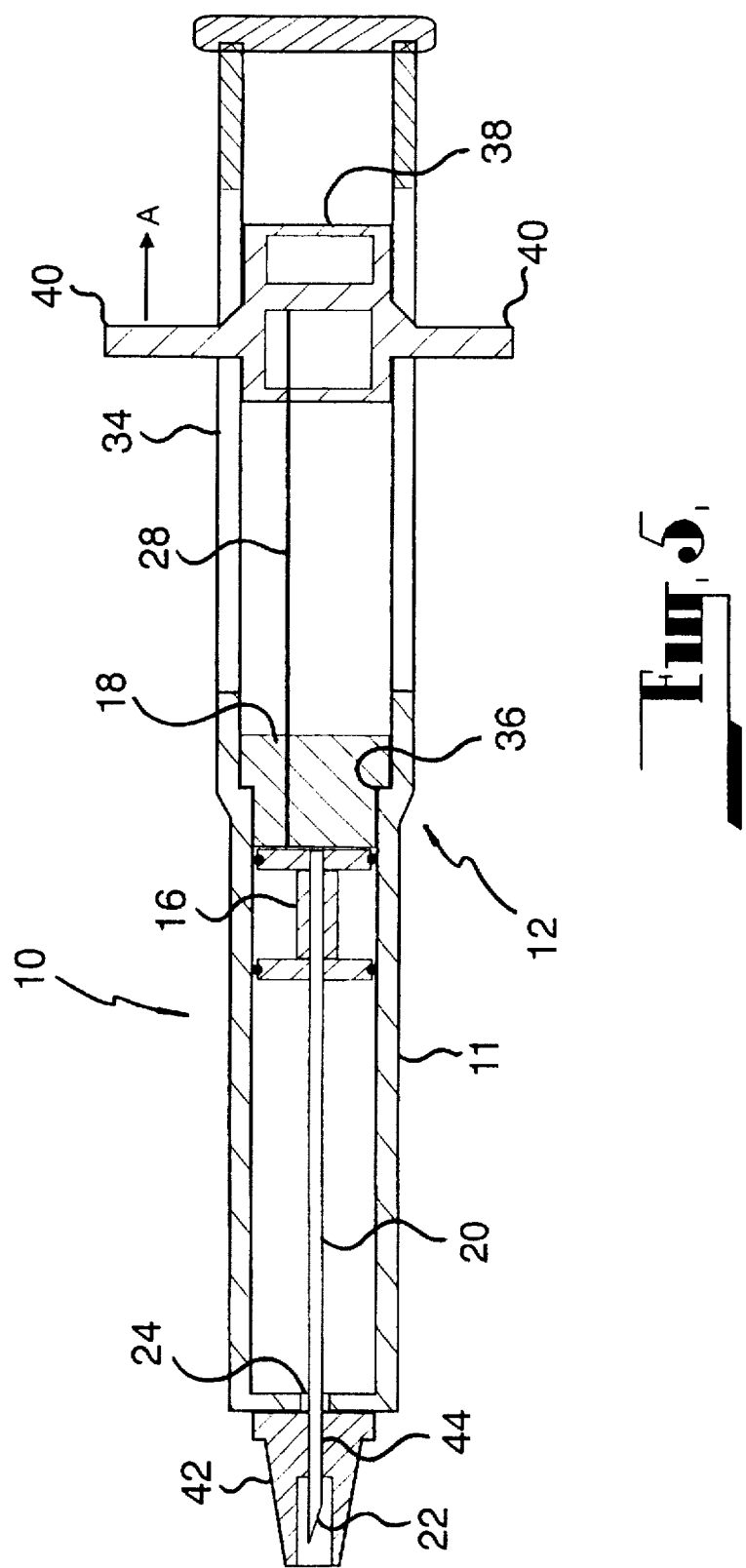
FIG. 5 is a sectional view of the embodiment of FIG. 1 prior to filling.
Figure 6:
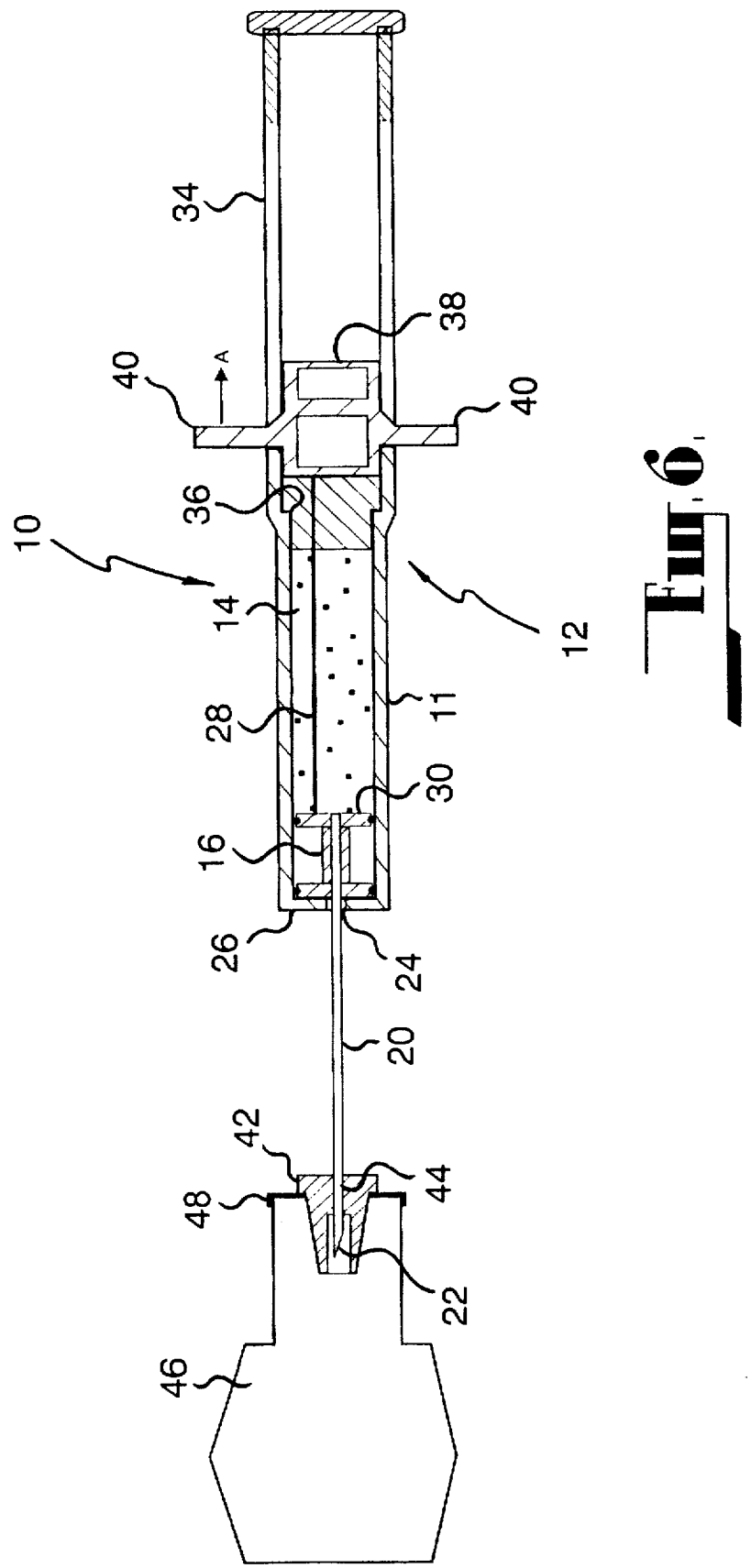
FIG. 6 is a sectional view of the embodiment of FIG. 1 at the conclusion of filling.

As shown in FIG. 5 and 6 a fresh unused syringe according to each of the embodiments can be provided with a rigid shaped nipple-like element 42 which is engaged in the opening 24 and with the free end of the nipple is engaged with the cover seal 48 of the ampoule. The needle is only partly retracted into the body such that its free end 22 extends from the opening 24. The engagement between the needle is such that the element 42 can be grasped by the user and pulled to cause the needle to be pulled to the fully extended position. The nipple-like element is the to receive a "Luer" or similar fitting. In addition, the outer end of the needle is configured such that it is able to pierced the seal of an ampoule. In each instance the frictional engagement affected with an ampoule may be sufficient to facilitate withdrawal of the needle.

The tight fit of the needle 20 within the seal 44 of the nipple is preferably sufficient to enable the needle 20 with the attached plug 16 to be moved to the extended position to cause the chamber 14 to be increased in volume. This results in the transfer of fluid into the chamber 14 to allow the filling of the chamber. On the full extension of the needle and with a greater force on the element 42, the needle 20 is withdrawn from within the nipple 42 to allow use of the needle when the needle has reached its outermost position.

In a seventh embodiment as shown at FIG. 11 a spring 52 or a like resilient device is provided within the space forward of the plug 16 between the plug and the forward end of the body 12. For example, a spring that is resiliently compressed to fill the chamber with parenteral fluid and is able to expand under its normal bias to reduce the volume of the chamber 14, may be suitable. A suitable trigger 54 is provided on the body 2 to hold the spring in its compressed state and to allow the release and subsequent expansion of the spring for injection. The trigger mechanism may be located externally of the body and is operatively connected with the spring through the forward wall of the body of the device.

In a further embodiment the resilient device referred to above is located within a space located rearward of the plug. In this alternative form, the resilient device can be a spring configured so as to be able to expand to fill the chamber with parenteral fluid and then resiliently to contract under its normal bias to reduce the volume of the chamber and expel the fluid. In such an arrangement, the flexible member referred to above may be secured to one end of the spring such that contraction of the spring moves the one end of the spring rearwardly to pull the plug rearwardly. Further, the spring is preferably configured so as to be able also to displace the stopping means in the same manner as described above. An appropriate trigger mechanism may again be utilised to control the actions of this rearwardly located spring.

Finally, the parenteral device of this invention may be marked with external graduations, according to normal practice, to assist in ensuring the administration of correct doses of parenteral fluid. This normal practice results in graduations from zero to a suitable number being included from the forward end of the device to the rearward end.

It will be appreciated that there may be other modifications and variations that may be made to the configurations described herein that are also within the scope of the present invention.

I claim:

1. A syringe comprising a tubular body having a forward end and a rearward end, the forward end being capable of receiving a hollow needle therein so as to be able to project therefrom, the needle being slidable relative to the body, the body also including a chamber capable of receiving a parenteral fluid and capable of being reduced in volume to expel the fluid contained therein, wherein; the needle is capable of being manually retracted into the body by a retracting means such that the chamber reduces in volume to expel the fluid contained therein and such that the needle is retracted to be wholly contained within the body; one end of the needle supported from the body by a plug which is slidably and sealingly received in the body, the chamber is located rearward of the plug and the plug is adapted to enable the needle to communicate with the chamber through the plug, a stop provided in the body rearward of the plug to define a rearward end of the camber, the stop being slidably and sealingly received in the body, whereby a greater degree of force is required to move the stop than to move the plug, the rearward end of the body slidably supporting a slider for axial slidable movement, an external protrusion on said slider for manipulation thereof to effect axial movement, said retracting means comprising a flexible member secured at one end to the plug and secured at the other end to the slider and slidably and sealingly received through the stop.

2. A syringe as claimed at claim 1, wherein the stop, when defining the rearward end of the chamber, is sealingly and slidably received in the body and on completion of the movement of the plug to the minimum volume position of the chamber, the stop is movable with the plug to a rearmost position where the stop will be accommodated in a non sealing manner in the rearward end of the body.

3. A syringe as claimed at claim 2, wherein the rearward end has a greater internal diameter than the remainder of the body.

4. A syringe as claimed at claim 3, wherein the stop when at its forward most position in the body, is located at the junction between the rearward end of the body and the remainder of the body.

5. A syringe as claimed at claim 4, wherein the junction is formed as a step in the internal wall of the body.

6. A syringe as claimed at claim 2, wherein the cross-sectional configuration of the rearward end of the body is formed with a portion of greater transverse dimension than the diameter of the remainder of the body.

7. A syringe as claimed at claim 6, wherein the plug, when at its rearmost position, is non sealingly received in the rearward end of the body.

8. A syringe as claimed at claim 6, wherein the external protrusion comprises an axial directed protrusion.

9. A syringe as claimed at claim 6, wherein the external protrusion comprises a radially directed protrusion.

10. A syringe as claimed at claim 6, wherein the stop, when at its forward most position in the body, is located at the junction between the rearward end of the body and the remainder of the body.

11. A syringe as claimed at claim 6, wherein a protrusion is provided within the body to pierce the stop on joint rearward movement of the stop and plug.

12. A syringe as claimed at claim 6, wherein the free end of the needle is received in a nipple-like element at the forward most end of the body whereby manual withdrawal of the nipple-like element away from the body will cause extension of the needle, said nipple-like element being removable from the needle.

13. A syringe as claimed at claim 2, wherein the plug, when at its rearmost position, is non sealingly received in the rearward end of the body.

14. A syringe as claimed at claim 2, wherein the external protrusion comprises an axial directed protrusion.

15. A syringe as claimed at claim 2, wherein the external protrusion comprises a radially directed protrusion.

16. A syringe as claimed at claim 2, wherein a protrusion is provided on the interior of the body which is engaged by the stop on the joint rearward movement of the stop and plug to cause damage to the sealing engagement between the body and the stop.

17. A syringe as claimed at claim 2, wherein a protrusion is provided within the body to pierce the stop on joint rearward movement of the stop and plug.

18. A syringe as claimed at claim 2, wherein the free end of the needle is received in a nipple-like element at the forward most end of the body whereby manual withdrawal of the nipple-like element away from the body will cause extension of the needle, said nipple-like element being removable from the needle.

19. A syringe as claimed at claim 18, wherein the nipple-like element is provided with a port which is engagable with a receptacle of a parenteral agent and the interior of the needle communicates with said port.

20. A syringe as claimed at claim 2, wherein a resilient means is provided between the body and the plug and is associated with a trigger means, said resilient means being in a stressed state when the needle is extended and whereby release of said trigger enables movement of the resilient means to an unstressed state, movement of the needle, plug and stop of the fully retracted position.

21. A syringe as claimed at claim 2, wherein a protrusion is provided on the interior of the body which is engaged by the plug on the joint rearward movement of the stop and plug to cause damage to the sealing engagement between the body and the plug.

22. A syringe as claimed at claim 2, wherein a protrusion is provided on the interior of the body which is engaged by the stop and the plug on the joint rearward movement of the stop and plug to cause damage to the sealing engagement between the body and the stop and the plug.

23. A syringe as claimed at claim 2, wherein a protrusion is provided within the body to pierce the plug on joint rearward movement of the stop and plug.

24. A syringe as claimed at claim 2, wherein a protrusion is provided within the body to pierce the stop and plug on joint rearward movement of the stop and plug.

* * * * *

UNITED STATES PATENT AND TRADEMARK OFFICE
CERTIFICATE OF CORRECTION

PATENT NO. : 5,762,633
DATED : JUNE 9, 1998
INVENTOR(S) : WHISSON

It is certified that error appears in the above-identified patent and that said Letters Patent is hereby corrected as shown below:

In the Abstract, line 13, change "retracting member" to —retracting mechanism—.

In the Abstract, line 23, change "forces" to —force is—.

In the Abstract, line 25, change "or axial" to —for axial—.

In the Abstract, line 27, change "retracting member" to —retracting mechanism—.

Column 5, line 51, delete "the" and insert —shaped—.

Column 6, line 10, delete "forward".

Column 6, line 52, change "camber" to —chamber—.

Column 7, line 2, insert —of the body— after "end".

Signed and Sealed this

Eighteenth Day of May, 1999

Attest:

Q. TODD DICKINSON

*Attesting Officer*   *Acting Commissioner of Patents and Trademarks*